United States Patent
Guile et al.

(10) Patent No.: US 7,345,047 B2
(45) Date of Patent: *Mar. 18, 2008

(54) SUBSTITUTED [1,2,3]TRIAZOLO[4,5-D]PYRIMIDINES

(75) Inventors: Simon Guile, Leicestershire (GB); Barrie Martin, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 353 days.

This patent is subject to a terminal disclaimer.

(21) Appl. No.: 11/008,895

(22) Filed: Dec. 10, 2004

(65) Prior Publication Data

US 2005/0143399 A1 Jun. 30, 2005

Related U.S. Application Data

(62) Division of application No. 10/399,748, filed as application No. PCT/SE01/02472 on Nov. 7, 2001, now Pat. No. 6,844,348.

(30) Foreign Application Priority Data

Nov. 9, 2000 (SE) .................................. 0004098-0

(51) Int. Cl.
 *C07D 487/04* (2006.01)
 *A61K 31/519* (2006.01)
 *A61P 7/02* (2006.01)

(52) U.S. Cl. ................... 514/261.1; 544/230; 544/254
(58) Field of Classification Search ............ 514/261.1; 544/230, 254
See application file for complete search history.

(56) References Cited

FOREIGN PATENT DOCUMENTS

WO    WO-99/05143 A1    2/1999

OTHER PUBLICATIONS

West, Anthony R., "Solid State Chemistry and its Applications," Wiley, New York, pp. 358 and 365 (1988).
Patricia Clutton et al., "Pharmacological Control of Platelet Function," Pharmacological Research 44(4):225-264 (2001).
Storey et al., "Open Multicentre Study of the P2T Receptor Antagonist AR-C69931MX Assessing Safety, Tolerability and Activity in Patients with Acute Coronary Syndromes," Thromb. Haemost., Medline Abstract PMID 11307804 85(3):401-407 (2001).

*Primary Examiner*—Brenda L. Coleman
*Assistant Examiner*—Susanna Moore
(74) *Attorney, Agent, or Firm*—Pepper Hamilton LLP

(57) ABSTRACT

The invention provides novel substituted cyclopentane compounds (in particular, substituted [1,2,3]triazolo[4,5-d]pyrimidines), their use as medicaments (in particular, their use as anti-thrombotic agents), compositions containing them and processes for their preparation.

16 Claims, No Drawings

SUBSTITUTED [1,2,3]TRIAZOLO[4,5-D]PYRIMIDINES

RELATED APPLICATIONS

This application is a divisional of U.S. application Ser. No. 10/399,748, filed on Apr. 21, 2003 now U.S. Pat. No. 6,844,348, which is a national stage filing under 35 U.S.C. 371 of International Application No. PCT/SE01/02472, filed Nov. 7, 2001, which claims priority from Sweden Patent Application No. 0004098-0, filed Nov. 9, 2000, the specifications of each of which are incorporated by reference herein. International Application No. PCT/SE01/02472 was published under PCT Article 21(2) in English.

FIELD OF THE INVENTION

The present invention provides novel substituted cyclopentane compounds, their use as medicaments, compositions containing them and processes for their preparation.

BACKGROUND OF THE INVENTION

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and platelet-mediated occlusion or re-occlusion also compromises angioplasty.

A number of converging pathways lead to platelet aggregation. Whatever the initial stimulus, the final common event is a cross-linking of platelets by binding of fibrinogen to a membrane-binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents. (The TIMI 9a Investigators (1994), *Circulation* 90, pp. 1624-1630; The Global Use of Strategies to Open Occluded Coronary Arteries (GUSTO) IIa Investigators (1994) *Circulation* 90, pp. 1631-1637; Neuhaus K. L. et. al. (1994) *Circulation* 90, pp. 1638-1642.).

It has been found that ADP acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81-106; Antiplatelet Trialists' Collaboration (1994), *Br. Med. J.* 308, pp. 159-168). Aspirin has no effect on aggregation produced by other sources of ADP, such as damaged cells or ADP released under conditions of turbulent blood flow. ADP-induced platelet aggregation is mediated by the $P_{2T}$ ($P2Y_{ADP}$ or $P2T_{AC}$) receptor subtype located on the platelet membrane. Recently it has been shown that antagonists at this receptor offer significant improvements over other anti-thrombotic agents. Accordingly there is a need to find $P_{2T}$ ($P2Y_{ADP}$ or $P2T_{AC}$) antagonists as anti-thrombotic agents.

DESCRIPTION OF THE INVENTION

In a first aspect the invention therefore provides a compound of formula (I),

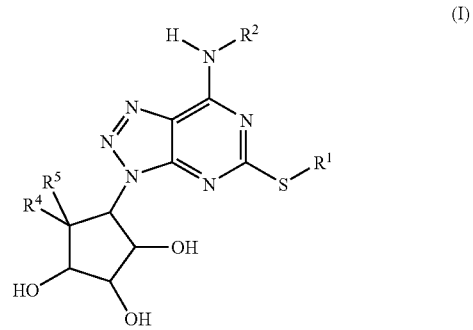

(I)

wherein:
$R^1$ is alkyl $C_{1-6}$ or alkenyl $C_{2-6}$, both independently optionally substituted by one or more groups selected from alkyl $C_{1-5}$ or halogen;
$R^2$ is cycloalkyl $C_{3-8}$, optionally substituted by $R^3$;
$R^3$ is phenyl, optionally substituted by one or more groups selected from alkyl $C_{1-6}$ or halogen;
$R^4$ and $R^5$ are alkyl $C_{1-6}$ or together cycloalkyl $C_{3-6}$;

or a pharmaceutically acceptable salt or solvate thereof, or a solvate of such a salt.

Preferably the compound of formula (I) has the following stereochemistry:

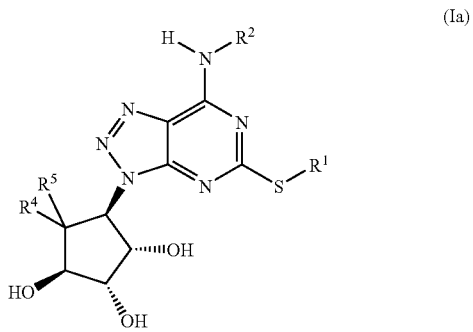

(Ia)

where $R^1$, $R^2$, $R^4$ and $R^5$ are as defined above.
Where $R^2$ is

the stereochemistry is preferably

Suitably, $R^1$ is alkyl optionally substituted by halogen.
Suitably, $R^2$ is cyclopropyl optionally substituted by $R^3$.
Suitably, $R^3$ is phenyl optionally substituted by halogen.
Suitably, $R^4$ and $R^5$ are cyclopropyl.

Particularly preferred compounds of the invention include:
(4S,5R,6S,7R)-7-[7-[[(1R,2S)-2-Phenylcyclopropyl]amino]-5-(propylthio)-3H-[1,2,3]triazolo[4,5-d]pyrimidin-3-yl]spiro[2.4]heptane-4,5,6-triol;

or a pharmaceutically acceptable salt or solvate thereof, or a solvate of such a salt.

According to the invention there is further provided a process for the preparation of a compound of formula (I) which comprises dihydroxylation of a compound of formula (II),

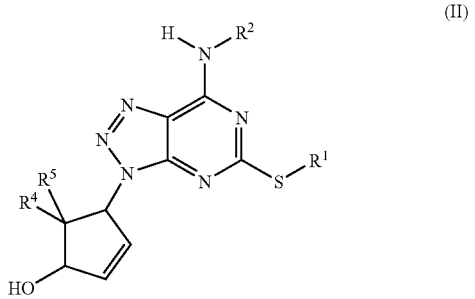

where $R^1$, $R^2$, $R^4$ and $R^5$ are as defined in formula (I), using osmium tetroxide in the presence of an oxidising agent, preferably N-methylmorpholine-N-oxide, and pyridine, in a solvent, preferably aqueous acetone, at a temperature between 20° C. and 100° C.

A compound of formula (II) can be prepared by removing the protecting group from a compound of formula (III),

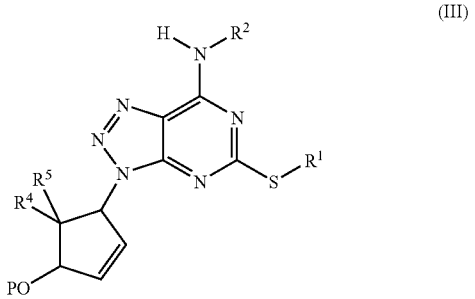

where $R^1$, $R^2$, $R^4$ and $R^5$ are as defined in formula (I) and P is a protecting group, preferably acetate. Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

A compound of formula (III) can be prepared by reacting a compound of formula (IV),

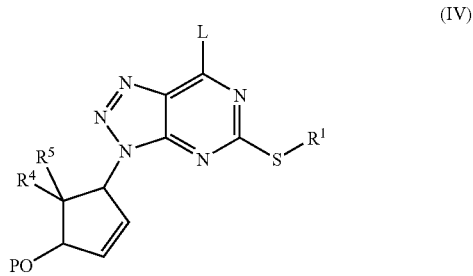

where $R^1$, $R^4$ and $R^5$ are as defined in formula (I), P is a protecting group, preferably acetate, and L is a leaving group, preferably halogen, with $R^2NH_2$ where $R^2$ is as defined in formula (I), in the presence of a base, preferably triethylamine or N,N-disopropylethylamine, in the presence of an inert solvent, preferably dichloromethane, at a temperature between 20° C. and 60° C.

A compound of formula (IV) can be prepared by reacting a compound of formula (V),

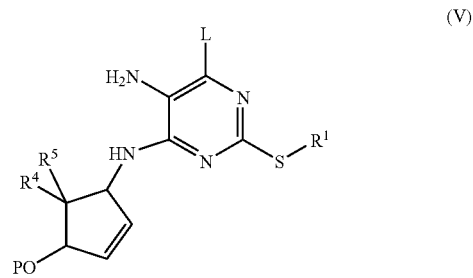

where $R^1$, $R^4$ and $R^5$ are as defined in formula (I) and P is a protecting group, preferably acetate, L is a leaving group, preferably halogen, with a $C_{1-6}$ alkyl nitrite, preferably iso-amylnitrite, in the presence of an inert solvent, preferably acetonitrile, at 20-80° C., or with an alkali metal nitrite, preferably sodium nitrite, under aqueous acidic conditions, preferably aqueous hydrochloric or acetic acid at a temperature between 0° C. and 20° C.

A compound of formula (V) can be prepared by reducing a compound of formula (VI),

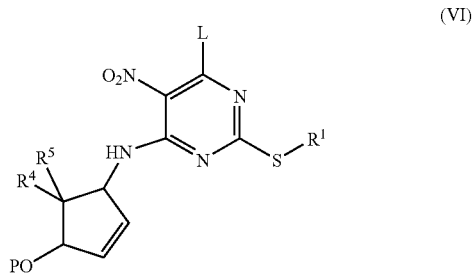

where $R^1$, $R^4$ and $R^5$ are as defined in formula (I), P is a protecting group, preferably acetate and L is a leaving group, preferably halogen, using, preferably, iron in an acidic solvent such as acetic acid, at a temperature between 20° C. and 80° C.

A compound of formula (VI) can be prepared by reacting a compound of formula (VII),

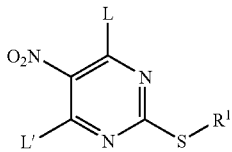

(VII)

where $R^1$ is as defined in formula (I), L is as defined above and L' is a leaving group, for example a halogen, where L and L' are preferably the same, with a compound of formula (VIII),

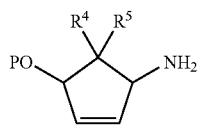

(VIII)

where $R^4$ and $R^5$ are as defined in formula (I) and P is a protecting group, preferably acetate, and a base, preferably triethylamine or N,N-disopropylethylamine, in the presence of an inert solvent, preferably tetrahydrofuran, at a temperature between 0° C. and 40° C.

A compound of formula (VIII) can be prepared by reducing a compound of formula (IX),

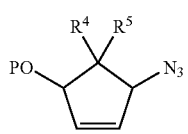

(IX)

where $R^4$ and $R^5$ are as defined in formula (I) and P is a protecting group, preferably acetate, with, for example, triphenylphosphine and water in the presence of an inert solvent, preferably tetrahydrofuran, at a temperature between 0° C. and 40° C.

A compound of formula (IX) can be prepared by reacting a compound of formula (X),

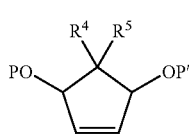

(X)

where $R^4$ and $R^5$ are as defined in formula (I), P is a protecting group, preferably acetate and P' is an acyl group, preferably acetyl, with a metal azide, preferably sodium azide using a catalyst, preferably a palladium(0) catalyst in the presence of a chiral ligand, preferably (−)-1,2-bis-N-[2'-(diphenylphosphino)benzoyl-1(S),2(S)-diaminocyclohexane, at a temperature between 0° C. and 40° C. Preferably P and P' are the same.

A compound of formula (X) can be prepared by oxidising a compound of formula (XI),

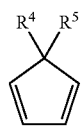

(XI)

where $R^4$ and $R^5$ are as defined in formula (I), preferably using a mixture of palladium acetate, lithium acetate, lithium chloride, manganese (IV) oxide and benzoquinone in acetic acid, water and tetrahydrofuran, at a temperature between 0° C. and 40° C.

All novel intermediates form a further aspect of the invention.

Salts of the compounds of formula (I) may be formed by reacting the free base, or a salt or a derivative thereof, with one or more equivalents of the appropriate acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, tetrahydrofuran or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_2T$ ($P2Y_{ADP}$ or $P2T_{AC}$) receptor antagonists. Accordingly, the compounds are useful in therapy, including combination therapy, particularly they are indicated for use as: inhibitors of platelet activation, aggregation and degranulation, promoters of platelet disaggregation, anti-thrombotic agents or in the treatment or prophylaxis of unstable angina, coronary revascularisation procedures including angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

According to the invention there is further provided the use of a compound according to the invention in the manufacture of a medicament for the treatment or prevention of the above disorders. In particular the compounds of the invention are useful for treating myocardial infarction, thrombotic stroke, transient ischaemic attacks, peripheral vascular disease and angina, especially unstable angina. The invention also provides a method of treatment or prevention of the above disorders which comprises administering to a patient suffering from such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution, which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

The invention is illustrated by the following examples. In the examples the NMR spectra were measured on a Varian Unity Inova 300 or 400 spectrometer. For examples which show the presence of rotamers in the proton NMR spectra only the chemical shifts of the major rotamer are quoted. MS spectra were obtained on Finnigan Mat SSQ7000 or a Micromass Platform spectrometer.

EXAMPLE 1

(4S,5R,6S,7R)-7-[7-[[(1R,2S)-2-Phenylcyclopropyl]amino]-5-(propylthio)-3H-[1,2,3]triazolo[4,5-d]pyrimidin-3-yl]spiro[2.4]heptane-4,5,6-triol a) (4R/S,7S/R)-Spiro[2.4]hept-5-ene-4,7diol diacetate To a two phase mixture of palladium acetate (1.7 g), lithium acetate dihydrate (123.6 g), lithium chloride (30.0 g), manganese (IV) oxide (15.3 g) and p-benzoquinone (1.4 g) in acetic acid (250 ml), water (420 ml) and pentane (3.7 l) was added spiro[2.4]hepta-4,6-diene (7.7 g) and the resulting mixture was stirred at ambient temperature for 24 hours. The reaction mixture was filtered through a celite plug washing with pentane (1 l). The organic phase was collected, washed successively with saturated sodium bicarbonate solution (500 ml), water (500 ml) and brine (100 ml) then concentrated to dryness under reduced pressure. The residue was absorbed onto silica and purified by chromatography ($SiO_2$; 9:1 isohexane:ethyl acetate) to afford the subtitle compound (2.1 g).

NMR δH ($CDCl_3$) 6.25 (2H, s), 5.25 (2H, s), 2.07 (6H, s), 1.01 (2H, t, J=8 Hz), 0.85 (2H, t, J=8 Hz).

b) (4R,7S)-7-Azidospiro[2.4]hept-5-en-4-ol acetate

To a solution of palladium-π-allyl chloride dimer (80 mg) and (−)-1,2-bis-N-[2'-(diphenylphosphino)benzoyl-1(S),2(S)-diaminocyclohexane (600 mg) in anhydrous tetrahydrofuran (25 ml) under nitrogen, was added a solution of the product of step a) (1.75 g) in tetrahydrofuran (25 ml) followed by a solution of sodium azide (560 mg) in water (10 ml). The resulting solution was stirred at ambient temperature for 45 minutes. The reaction mixture was passed through a plug of silica washing with ethyl acetate (50 ml) and then concentrated to dryness under reduced pressure. The residue was the purified by chromatography (SiO$_2$; 12:1 isohexane:ethyl acetate) to afford the subtitle compound (0.85 g).

NMR δH (CDCl$_3$) 6.29 (1H, dd, J=6 Hz, 2 Hz), 6.22 (1H, dd, J=6 Hz, 2 Hz), 5.23 (1H, d, J=2 Hz), 3.56 (1H, s), 2.07 (3H, s), 0.86-1.06 (4H, m).

c) (4R,7S)-7-Aminospiro[2.4]hept-5-en-4-ol acetate

A solution of the product of step b) (0.85 g) and triphenylphosphine (1.46 g) in tetrahydrofuran (5 ml) and water (1 ml) was stirred at ambient temperature under nitrogen for 64 hours. The reaction mixture was concentrated to dryness under reduced pressure azeotroping with toluene (2×50 ml) and purified by chromatography (SiO$_2$; 97:2:1 ethyl acetate: methanol:ammonia) to afford the subtitle compound (0.67 g).

NMR δH (CDCl$_3$) 6.26 (1H, dd, J=5 Hz, 2 Hz), 6.00 (1H, dd, J=5 Hz, 2 Hz), 5.22 (1H, d, J=2 Hz), 3.30 (1H, s), 2.07 (3H, s), 0.74-0.82 (4H, m).

d) (4R,7S)-7-[[6-Chloro-5-nitro-2-(propylthio)-4-pyrimidin-4-yl]amino]spiro[2.4]hept-5-en-4-ol acetate To a solution of 4,6-dichloro-5-nitro-3-propylthiopyrimidine (prepared as described in WO 9703084) (2.1 g) and N,N-diisopropylethylamine (1 ml) in anhydrous tetrahydrofuran (10 ml) was added a solution of the product from step c) (0.67 g) in tetrahydrofuran (10 ml). The reaction was stirred at ambient temperature for 2 hours then absorbed onto silica and purified by chromatography (SiO$_2$; 95:5 isohexane:ethyl acetate) to afford the subtitle compound (1.25 g).

NMR δH (CDCl$_3$) 8.00 (1H, d, J=9 Hz), 6.28 (1H, dd, J=6 Hz, 2 Hz), 6.24 (1H, dd, J=6 Hz, 2 Hz), 5.19 (1H, d, J=2 Hz), 4.91 (1H, dd, J=9 Hz, 2 Hz), 3.06 (2H, t, J=7 Hz), 2.07 (3H, s), 1.74 (2H, sex, J=7 Hz), 1.01 (3H, t, J=7 Hz), 0.97-1.09 (2H, m), 0.89 (1H, dt, J=10 Hz, 6 Hz), 0.77 (1H, dt, J=10 Hz, 6 Hz).

e) (4R,7S)-7-[[5-Amino-6-chloro-2-(propylthio)-4-pyrimidin-4-yl]amino]spiro[2.4]hept-5-en-4-ol acetate Iron powder (1.2 g) was added to a stirred solution of the product of step d) (1.2 g) in acetic acid (20 ml). The reaction mixture was stirred at room temperature for 2 hours, concentrated to half volume, neutralised with saturated aqueous sodium bicarbonate, diluted with ethyl acetate and washed with water. The organic phase was dried and concentrated to afford the subtitle compound (1.15 g).

NMR δH (CDCl$_3$) 6.26 (1H, dd, J=6 Hz, 3 Hz), 6.15 (1H, dd, J=6 Hz, 1 Hz), 5.19 (1H, d, 10 Hz), 5.18 (1H, d, J=3 Hz), 4.90 (1H, dd, J=10 Hz, 1 Hz), 3.10 (2H, bs), 3.01 (2H, t, J=7 Hz), 2.06 (3H, s), 1.72 (2H, sex, J=7 Hz), 1.00 (3H, t, J=7 Hz), 0.98-1.10 (2H, m), 0.70-0.80 (2H, m).

f) (4R,7S)-7-[7-Chloro-5-(propylthio)-3H-[1,2,3]triazolo[4,5-d]pyrimidin-3-yl]spiro[2.4]hept-5-en-4-ol acetate Isoamyl nitrite (0.5 ml) was added to a solution of the product of step e) (1.1 g) in acetonitrile (30 ml) and the solution was heated at 70° C. for 1 hour. The cooled reaction mixture was concentrated and purified by chromatography (SiO$_2$; dichloromethane) to afford the subtitle compound (0.9 g).

NMR δH (CDCl$_3$) 6.50 (1H, dt, J=6 Hz, 2 Hz), 6.39 (1H, dd, J=6 Hz, 2 Hz), 5.59 (1H, t, J=2 Hz), 5.51 (1H, d, 2 Hz), 3.25 (1H, dt, J=3 Hz, 1 Hz), 3.08 (2H, dt, J=7 Hz, 1 Hz), 2.05 (3H, s), 1.81 (2H, sex, J=7 Hz), 1.15-1.22 (2H, m), 1.08 (3H, t, J=7 Hz), 0.70-0.85 (2H, m), 0.00-0.25 (2H, m).

g) (4R,7S)-7-[5-(Propylthio)-7-[[(1R,2S)-2-phenyl-cyclopropyl]amino]-3H-1,2,3-triazolo[4,5-d]pyrimidin-3-yl]-spiro[2.4]hept-5-en-4-ol Acetate To a solution of the product of step f) (0.5 g) and (1R-trans)-2-phenyl-cyclopropanamine, [R-(R*,R*)]-2,3-dihydroxybutanedioate (1:1) (prepared as described by L. A. Mitscher et al., J. Med. Chem. 1986, 29, 2044) (0.4 g) in dichloromethane (50 ml) was added N,N-diisopropylethylamine (2 ml) and the resulting solution was stirred and heated at reflux for 3 hours. The reaction mixture was concentrated to dryness under reduced pressure and purified by chromatography (SiO$_2$; 4:1 isohexane:ethyl acetate) to give the subtitle compound (0.6 g).

MS (APCI) 477 (M+H$^+$, 100%).

h) (4R,7S)-7-[5-(Propylthio)-7-[[(1R,2S)-2-phenyl-cyclopropyl]amino]-3H-1,2,3-triazolo[4,5-d]pyrimidin-3-yl]-spiro[2.4]hept-5-en-4-ol To a solution of the product of step g) (0.5 g) in methanol (10 ml) was added potassium carbonate (0.5 g) and the resulting suspension was stirred at ambient temperature for 2 hours. The reaction mixture was absorbed onto silica and purified by chromatography (SiO$_2$; 3:1 isohexane:ethyl acetate) to give the subtitle compound (0.4 g).

MS (APCI) 435 (M+H$^+$), 389 (100%).

i) (4S,5R,6S,7R)-7-[7-[[(1R,2S)-2-Phenylcyclopropyl]amino]-5-(propylthio)-3H-[1,2,3]triazolo[4,5-d]pyrimidin-3-yl]spiro[2.4]heptane-4,5,6-triol A solution of the product of step h) (0.4 g), N-methylmorpholine-N-oxide (0.19 g), pyridine (75 μl) and osmium tetraoxide (2.5% weight solution of in t-butanol; 140 μl) in acetone (15 ml) and water (5 ml) was heated at reflux for 4 hours. To the cooled reaction mixture was added sodium metabisulphite (0.3 g) and after stirring for 1 hour the suspension was filtered through a plug of silica, washing with methanol (50 ml). The residue was absorbed onto silica and purified by chromatography (SiO$_2$; ethyl acetate) to give the title compound (0.34 g).

NMR δH (d$_6$-DMSO) 9.36 (1H, d, J=5 Hz), 7.29 (2H, t, J=7 Hz), 7.21-7.16 (3H, m), 5.17 (1H, d, J=6 Hz), 5.05 (1H, d, J=3 Hz), 5.01-4.97 (2H, m), 4.96 (1H, d, J=3 Hz), 3.93 (1H, bs), 3.53 (1H, bs), 3.20-3.17 (1H, m), 2.96 (1H, dt, J=14 Hz, 7 Hz), 2.80 (1H, dt, J=14 Hz, 7 Hz), 2.16-2.12 (1H, m), 1.55-1.44 (3H, m), 1.34-1.24 (1H, m), 0.82 (2H, t, J=7 Hz), 0.73-0.70 (1H, m), 0.64-0.60 (1H, m), −0.60--0.70 (1H, m).

Pharmacological Data

The preparation for the assay of the P$_{2T}$(P2Y$_{ADP}$ or P2T$_{AC}$) receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125 G followed by further centrifugation for 15 minutes at 640 G.

The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C. Following addition of a further 300 ng/ml PGI$_2$, the pooled suspension was centrifuged once more for 15 minutes at 640 G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 µl of 50 mM solution with a final concentration of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 µl of 10 mg/ml solution of clottable protein in saline) and 300 nM (10 µl of 15 mM solution in 6% glucose), respectively. Platelets or buffer as appropriate were added in a volume of 150 µl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 µl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 µl of 450 mM) was then added to each well and the plate shaken for a further 5 min before reading the absorbance again at 660 nm.

Antagonist potency was estimated as a % inhibition of the control ADP response to obtain an IC$_{50}$. Compounds exemplified have pIC$_{50}$ values of more than 5.0.

The invention claimed is:

1. A compound of formula II

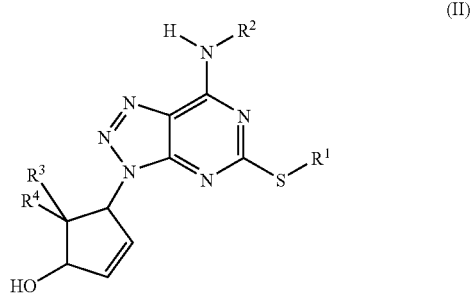

(II)

wherein:
R$^1$ is alkyl C$_{1-6}$ or alkenyl C$_{2-6}$, both independently optionally substituted by one or more groups selected from alkyl C$_{1-5}$ or halogen;
R$^2$ is cycloalkyl C$_{3-8}$, optionally substituted by R$^3$;
R$^3$ is phenyl, optionally substituted by one or more groups selected from alkyl C$_{1-6}$ or halogen;
R$^4$ is alkyl C$_{1-6}$; and
R$^5$ is alkyl C$_{1-6}$;
or, together, R$^4$ and R$^5$ are cycloalkyl C$_{3-6}$.

2. A compound according to claim 1 wherein R$^1$ is alkyl C$_{1-6}$ optionally substituted by halogen.

3. A compound according to claim 1 wherein, together, R$^4$ and R$^5$ are cyclopropyl.

4. A compound according to claim 1 wherein R$^2$ is cyclopropyl optionally substituted by R$^3$.

5. A compound according to claim 4 wherein R$^2$ is

6. A compound according to claim 4 wherein R$^3$ is phenyl optionally substituted by halogen.

7. A compound of formula III

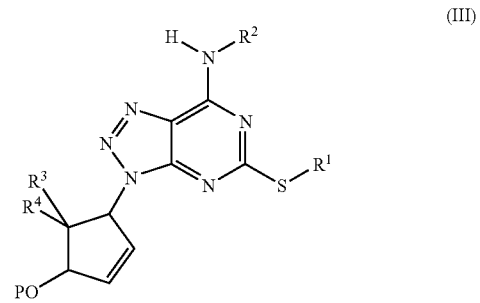

(III)

wherein:
R$^1$ is alkyl C$_{1-6}$ or alkenyl C$_{2-6}$, both independently optionally substituted by one or more groups selected from alkyl C$_{1-5}$ or halogen;
R$^2$ is cycloalkyl C$_{3-8}$, optionally substituted by R$^3$;
R$^3$ is phenyl, optionally substituted by one or more groups selected from alkyl C$_{1-6}$ or halogen;
R$^4$ is alkyl C$_{1-6}$;
R$^5$ is alkyl C$_{1-6}$;
or, together, R$^4$ and R$^5$ are cycloalkyl C$_{3-6}$; and
P is a protecting group.

8. A compound according to claim 7 wherein R$^1$ is alkyl C$_{1-6}$ optionally substituted by halogen.

9. A compound according to claim 7 wherein, together, R$^4$ and R$^5$ are cyclopropyl.

10. A compound according to claim 7 wherein R$^2$ is cyclopropyl optionally substituted by R$^3$.

11. A compound according to claim 10 wherein R$^2$ is

12. A compound according to claim 10 wherein R³ is phenyl optionally substituted by halogen.

13. A compound of formula IV

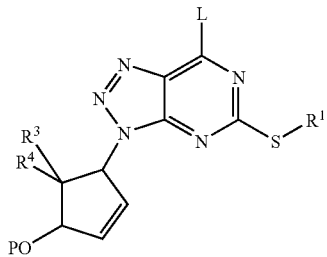

(IV)

wherein:
R¹ is alkyl $C_{1-6}$ or alkenyl $C_{2-6}$, both independently optionally substituted by one or more groups selected from alkyl $C_{1-5}$ or halogen;
R² is cycloalkyl $C_{3-8}$, optionally substituted by R³;
R⁴ is alkyl $C_{1-6}$;
R⁵ is alkyl $C_{1-6}$;
or, together, R⁴ and R⁵ are cycloalkyl $C_{3-6}$;
P is a protecting group; and
L is a leaving group.

14. A compound according to claim 13 wherein L is halogen.

15. A compound according to claim 13 or claim 14 wherein R¹ is alkyl $C_{1-6}$ optionally substituted by halogen.

16. A compound according to claim 13 or claim 14 wherein, together, R⁴ and R⁵ are cyclopropyl.

* * * * *